United States Patent
Kharrat et al.

(10) Patent No.: US 9,041,933 B2
(45) Date of Patent: May 26, 2015

(54) SYSTEM AND METHOD FOR CHARACTERIZING CRUDE OIL FRACTIONS

(71) Applicant: Schlumberger Technology Corporation, Sugar Land, TX (US)

(72) Inventors: Abdel M. Kharrat, Edmonton (CA); Farshid Mostowfi, Edmonton (CA)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 0 days.

(21) Appl. No.: 14/349,066

(22) PCT Filed: Mar. 1, 2013

(86) PCT No.: PCT/US2013/028523
§ 371 (c)(1),
(2) Date: Apr. 1, 2014

(87) PCT Pub. No.: WO2013/130932
PCT Pub. Date: Sep. 6, 2013

(65) Prior Publication Data
US 2015/0036136 A1 Feb. 5, 2015

Related U.S. Application Data

(60) Provisional application No. 61/605,348, filed on Mar. 1, 2012.

(51) Int. Cl.
*G01N 33/28* (2006.01)
*E21B 49/10* (2006.01)
(Continued)

(52) U.S. Cl.
CPC ............ *G01N 33/28* (2013.01); *G01N 33/2823* (2013.01); *G01N 21/05* (2013.01);
(Continued)

(58) Field of Classification Search
None
See application file for complete search history.

(56) References Cited

U.S. PATENT DOCUMENTS 4,493,765 A * 1/1985 Long et al. ............... 208/309
4,683,005 A 7/1987 Poirier
(Continued)

FOREIGN PATENT DOCUMENTS

WO 2011/030243 3/2011

OTHER PUBLICATIONS

L. Carbognani, E. Buenrostro-Gonzalez, "Oxidation Evidenced during Hydrogen Preparative Fractionation Isolation," Intrinsic Stability Aspects Affecting Crude Oils, Energy & Fuels, 20, 2006, pp. 1137-1144.

(Continued)

*Primary Examiner* — Kara E Geisel
*Assistant Examiner* — Jarreas C Underwood
(74) *Attorney, Agent, or Firm* — Daren C. Davis; Wayne I. Kanak

(57) ABSTRACT

A system for characterizing crude oil fractions includes a maltenes sample reservoir, a first solvent reservoir, a second solvent reservoir, and a third solvent reservoir. The system further includes a valve in fluid communication with the first solvent reservoir, the second solvent reservoir, and the third solvent reservoir and a pump in fluid communication with the valve. The system further includes a packed bed in fluid communication with the maltenes sample reservoir and the pump, a flowthrough cell in fluid communication with the packed bed, a spectrometer operably associated with the flowthrough cell, and a computer operably associated with the spectrometer. A method for characterizing crude oil fractions includes providing a maltene sample, eluting saturates, aromatics, and resins of the maltene sample, determining an optical density of each, and determining a concentration of each of the saturates, aromatics, and resins based upon optical densities over time for each.

23 Claims, 7 Drawing Sheets

(51) Int. Cl.
*G01N 21/3577* (2014.01)
*G01N 21/59* (2006.01)
*G01N 21/85* (2006.01)
*G01N 21/25* (2006.01)
*G01N 21/05* (2006.01)

(52) U.S. Cl.
CPC ............ *G01N21/3577* (2013.01); *G01N 21/59* (2013.01); *G01N 21/85* (2013.01); *G01N 21/25* (2013.01); *G01N 2201/061* (2013.01)

(56) References Cited

U.S. PATENT DOCUMENTS

| | | | |
|---|---|---|---|
| 4,843,247 A * | 6/1989 | Yamazoe et al. | 250/573 |
| 5,192,420 A | 3/1993 | Ohta et al. | |
| 5,672,873 A * | 9/1997 | Yamazoe | 250/339.12 |
| 8,805,617 B2 * | 8/2014 | Zuo et al. | 702/11 |
| 8,951,410 B2 * | 2/2015 | Koseoglu et al. | 208/302 |
| 8,996,346 B2 * | 3/2015 | Zuo et al. | 703/10 |
| 2002/0139929 A1 | 10/2002 | Mullins et al. | |
| 2011/0066441 A1 | 3/2011 | Ovalles et al. | |
| 2013/0067991 A1* | 3/2013 | Schabron et al. | 73/23.37 |
| 2014/0369889 A1* | 12/2014 | Mostowfi et al. | 422/82.09 |
| 2014/0375991 A1* | 12/2014 | Schneider et al. | 356/326 |

OTHER PUBLICATIONS

J.M. Chaffin, et al, "The Use of HPLC to Determine the Saturate Content of Heavy Petroleum Products," Journal of Liquid Chromatography and Related Technology, 19, 1996, pp. 1669-1882.

T. Fan, J.S. Buckley, "Rapid and Accurate SARA Analysis of Medium Gravity Crude Oils," Energy & Fuels, 16, 2002, pp. 1571-1575.

B.J. Fuhr, et al, "5th International conference on Petroleum Phase Behavior and Fouling," Banff, Canada, Jun. 13-17, 2004, "Comparison of Bitumen Fractionation Methods".

P.L. Grizzle, D.M. Sablotny, "Automated Liquid Chromatographic Compound Class Group-Type Separation of Crude Oils and Bitumens Using Chemically Bonded Aminosilane," Analytical Chemistry, 58, 1986, pp. 2389-2396.

D.M. Jewell, et al, "Ion-Exchange, Coordination, and Adsorption Chromatographic Separation of Heavy-End Petroleum Distillates," Analytical Chemistry, 44, 1972, pp. 1391-1395.

K. Karan, et al., "Systematic Evaluation of Asphaltenes Instability and Control During Production of Live Oils: A Flow Assurance Study," Petroleum Science and Technology, 21, 2003, pp. 629-645.

R. Miller, "Hydrocarbon Class Fractionation with Bonded-Phase Liquid Chromatography," Analytical Chemistry 54, 1982, pp. 1742-1746.

A. Pina, et al, "Characterization of Asphaltenes and Modeling of Flocculation—State of the Art.," Oil & Gas Science and Technology, 61, 2006, pp. 319-343.

M. Radke, et al, "Class Separation of Aromatic Compounds in Rock Extracts and Fossil Fuels by Liquid Chromatography," Analytical Chemistry, 56, 1984, pp. 2538-2546.

J.C. Suatoni, R.E. Swab, "Rapid Hydrocarbon Group-Type Analysis by High Performance Liquid Chromatography," Journal of Chromatographic Science, 13, 1975, pp. 361-366.

* cited by examiner

SYSTEM AND METHOD FOR CHARACTERIZING CRUDE OIL FRACTIONS

BACKGROUND

Characterization of fluids within an oilfield reservoir is desirable, if not necessary, for many reasons. For example, the behavior of a fluid within the reservoir depends upon its composition. Modeling this behavior with time typically requires the results of compositional analyses along with the knowledge of other physical parameters. Proper reservoir management requires the knowledge of reservoir conditions, such as pressure, temperature, and the like, in addition to the composition of the fluid within the reservoir. During transportation and storage, the mixing of different fluids can cause perturbation of the fluids system. The presence of incompatible fluids can lead to precipitation and deposition of such precipitates on components of the fluid transportation system. The refining process is also dependent upon the nature and makeup of the reservoir fluids being refined. To characterize such reservoir fluids, the fluids are commonly separated into saturates, aromatics, resins, and asphaltenes, or "SARA" fractions.

Conventional methods employed to separate reservoir fluids into these fractions require large quantities of solvents, are time consuming and operator dependent, and are not practical to use in the field. Such conventional methods typically require a significant inventory of tools and glassware, including evaporators and a fume hood. Moreover, equipment required to perform these conventional methods occupies a large footprint, which limits the mobility of the technique. Furthermore, cross-contamination is common, wherein one fraction is not completely separated, resulting in contamination of other fractions. Conventional separation methods also suffer from poor repeatability and reproducibility.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, a system for characterizing crude oil fractions includes a maltenes sample reservoir, the maltene fraction being the fraction of oil remaining after precipitation and removal of the asphaltene fraction, i.e. saturates, aromatics, and resins, a first solvent reservoir, a second solvent reservoir, and a third solvent reservoir. The system further includes a valve or valves in fluid communication with the first solvent reservoir, the second solvent reservoir, and the third solvent reservoir and a pump or pumps in fluid communication with the valve or valves. The system further includes a packed bed in fluid communication with the maltenes sample reservoir and the pump or pumps, a flowthrough cell in fluid communication with the packed bed, a light source and spectrometer operably associated with the flowthrough cell, and a computer operably associated with the spectrometer.

In another aspect, a method for characterizing crude oil fractions includes providing a maltene sample, eluting saturates of the maltene sample, and determining an optical density of the saturates at a predetermined wavelength as they pass through the flowthrough cell. The method further includes eluting aromatics of the maltene sample, determining an optical density of the aromatics at a predetermined wavelength as they pass through the flowthrough cell, and eluting resins of the maltene sample, and determining an optical density of the resins at a predetermined wavelength as they pass through the flowthrough cell. The method further includes determining a concentration of each of the eluted saturates, the eluted aromatics, and the eluted resins based upon optical densities over time for each of the eluted saturates, the eluted aromatics, and the eluted resins.

In yet another aspect, a method for characterizing crude oil fractions includes providing a maltene sample, eluting saturates of the maltene sample using a packed bed, such as may contain alumina or silica, and an eluent, such as n-heptane, and determining optical densities at a predetermined wavelength over time for the saturates as the saturates of the maltene sample are eluted in the packed bed. The method further includes eluting aromatics of the maltene sample using a packed bed, such as may contain alumina or silica, an eluent, such as toluene, and determining optical densities at a predetermined wavelength over time for the aromatics as the aromatics of the maltene sample are eluted in the packed bed. Yet further, the method includes eluting resins of the maltene sample using a packed bed, such as may contain alumina or silica, and an eluent, such as a mixture of dichloromethane and methanol, and determining optical densities at a predetermined wavelength over time for the resins as the resins of the maltene sample are eluted in the packed bed. A concentration is determined for each of the eluted saturates, the eluted aromatics, and the eluted resins based upon optical densities over time for each of the eluted saturates, the eluted aromatics, and the eluted resins.

BRIEF DESCRIPTION OF THE DRAWINGS

Embodiments of the disclosed subject matter of the application are described with reference to the following figures. The same numbers are used throughout the figures to reference like features and components.

Figure 1:
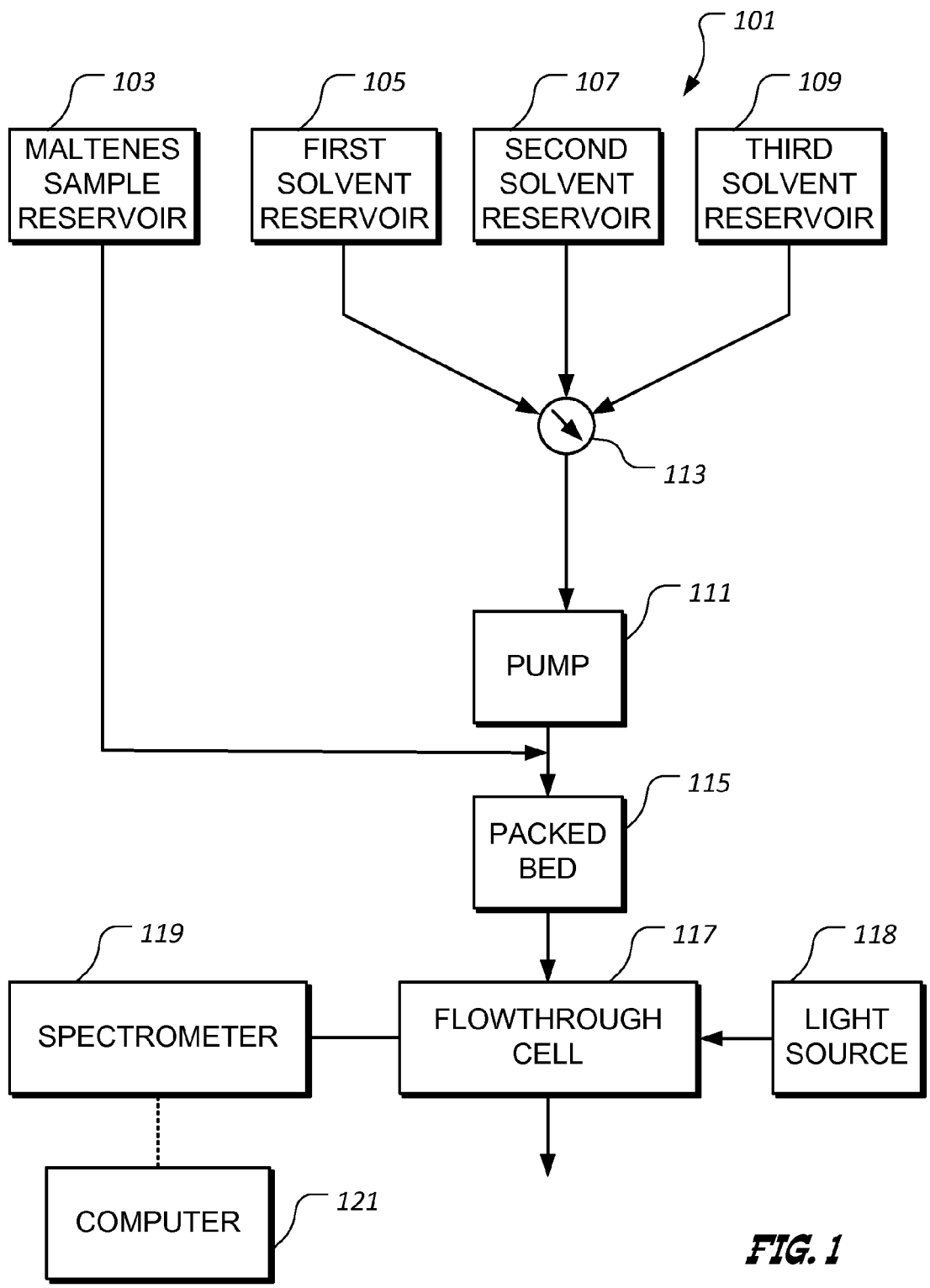
FIG. 1 is a schematic representation of a first illustrative embodiment of a system for characterizing crude oil fractions.

While the disclosed subject matter of the application is susceptible to various modifications and alternative forms, specific embodiments thereof have been shown by way of example in the drawings and are herein described in detail. It should be understood, however, that the description herein of specific embodiments is not intended to limit the disclosed subject matter of the application to the particular forms disclosed, but on the contrary, the intention is to cover all modifications, equivalents, and alternatives falling within the scope of the disclosed subject matter of the application as defined by the appended claims.

DETAILED DESCRIPTION

Illustrative embodiments of the disclosed subject matter of the application are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

The disclosed subject matter of the application relates to the characterization of saturate, aromatic, and resin fractions in a petroleum crude oil using optical spectroscopy techniques in the ultraviolet and visible spectral ranges and the temporal response of optical density measurement techniques.

Petroleum crude oils exhibit colors, such as yellow, brown, or black. The color originates from the electronic absorption edge of large molecules, such as saturates, aromatics, resins, and asphaltenes. Generally, the larger a crude oil molecule, the darker the color exhibited by the crude oil molecule. The color indicates absorption of light in the ultraviolet and visible ranges.

FIG. 1 depicts a schematic representation of an illustrative embodiment of a system 101 for determining saturate, aromatic, and resin fractions in a petroleum crude oil sample using optical spectroscopy. Specifically, system 101 determines these fractions in the maltenes portion of the crude oil sample, that is, in the portion of the sample from which the asphaltenes have been removed. In the illustrated embodiment, system 101 comprises a maltenes sample reservoir 103, a first solvent reservoir 105, a second solvent reservoir 107, and a third solvent reservoir 109. First solvent reservoir 105, second solvent reservoir 107, and third solvent reservoir 109 are in fluid communication with a pump 111 via a valve 113. It should be noted that valve 113 may be replaced by as many as three independent valves and multiple independent pumps may be used in place of pump 111, in which case valve or valves 113 may be omitted. Maltenes sample reservoir 103 is in fluid communication with a packed bed 115, as is pump 111, and the packed bed 115 is in further fluid communication with a flowthrough cell 117. Flowthrough cell 117 is operably associated with a light source 118 and a spectrometer 119, which is also operably associated with a computer 121.

Maltenes sample reservoir 103 is configured to store a sample of maltenes, that is, a sample of crude oil from which the asphaltenes have been removed. First solvent reservoir 105 is configured to store a solvent that is suitable to elute saturates of the maltenes, for example n-heptane or the like. Second solvent reservoir 107 is configured to store a solvent that is suitable to elute aromatics of the maltenes, for example toluene or the like. Third solvent reservoir 109 is configured to store a solvent that is suitable to elute resins of the maltenes, for example a mixture of dichloromethane and methanol, which may be a mixture comprising about 50 percent by volume dichloromethane and about 50 percent by volume methanol, or the like. Pump 111 is configured to selectively urge solvent from one of solvent reservoirs 105, 107, and 109 depending upon the state of valve 113. Pump 111 selectively urges solvent into packed bed 115. Packed bed 115 is, in one embodiment, a column of packed alumina or silica, for example, exhibiting a grain size within a range of about 80 mesh to about 200 mesh, having an inlet in fluid communication with pump 111 and an outlet in fluid communication with flowthrough cell 117. In one embodiment, flowthrough cell 117 incorporates a cuvette, such as a cuvette having a light path of about five millimeters and a volume of about 195 microliters, such as is available from Starna Cells, Inc. of Atascadero, Calif., USA. Spectrometer 119, in one embodiment, is a model HR 2000, with an associated model DT-mini 2B light source 118, available from Ocean Optics, Inc. of Dunedin, Fla., USA. Computer 121 may be, in various embodiments, any suitable computer configured to process data generated by spectrometer 119, such as a microcomputer or the like. In one embodiment, computer 121 operates analysis software, for example Spectra Suite software available from Ocean Optics, Inc.

Still referring to FIG. 1, packed bed 115 is, in an embodiment wherein packed bed 115 is a column of packed alumina, prepared by activating alumina in a furnace having a temperature of about 430° C. for a period of about 24 hours. The alumina is then cooled to ambient temperature in a desiccator and introduced into the column and wetted using n-heptane, or the like.

In a first particular operation of system 101, valve 113 is set so that first solvent reservoir 105 is in fluid communication with pump 111. Pump 111 then urges the first solvent from first solvent reservoir 105 into packed bed 115 to elute the saturates of the maltenes portion in packed bed 115. The saturates are routed to flowthrough cell 117, such that spectrometer 119 measures the optical density of the saturates at a predetermined wavelength, transmitting the data to computer 121. After the saturates have been eluted from the packed bed, valve 113 is set so that second solvent reservoir 107 is in fluid communication with pump 111. Pump 111 then urges the second solvent from second solvent reservoir 107 into packed bed 115 to elute the aromatics of the maltenes portion. The aromatics are routed to flowthrough cell 117, such that spectrometer 119 measures the optical density of the aromatics at a predetermined wavelength, transmitting the data to computer 121. After the aromatics have been eluted from the packed bed, valve 113 is set so that third solvent reservoir 109 is in fluid communication with pump 111. Pump 111 then urges the third solvent from third solvent reservoir 109 into packed bed 115 to elute the resins of the maltenes portion. The resins are routed to flowthrough cell 117, such that spectrometer 119 measures the optical density of the resins at a predetermined wavelength, transmitting the data to computer 121.

In one embodiment, spectrometer 119 measures the optical density of the saturates, aromatics, and resins of the maltenes, and thus the crude oil sample from which the maltenes are separated, at wavelengths of about 285 nanometers, about 470 nanometers, and about 600 nanometers, respectively. In one particular operation, the optical density of each of the saturates, aromatics, and resins were measured at a wavelength of about 800 nanometers. The 800 nanometer measurements were then subtracted from the measurements at about 285 nanometers, about 470 nanometers, and about 600 nanometers to minimize background interference and baseline shift and yield differential optical density.

Figure 2:
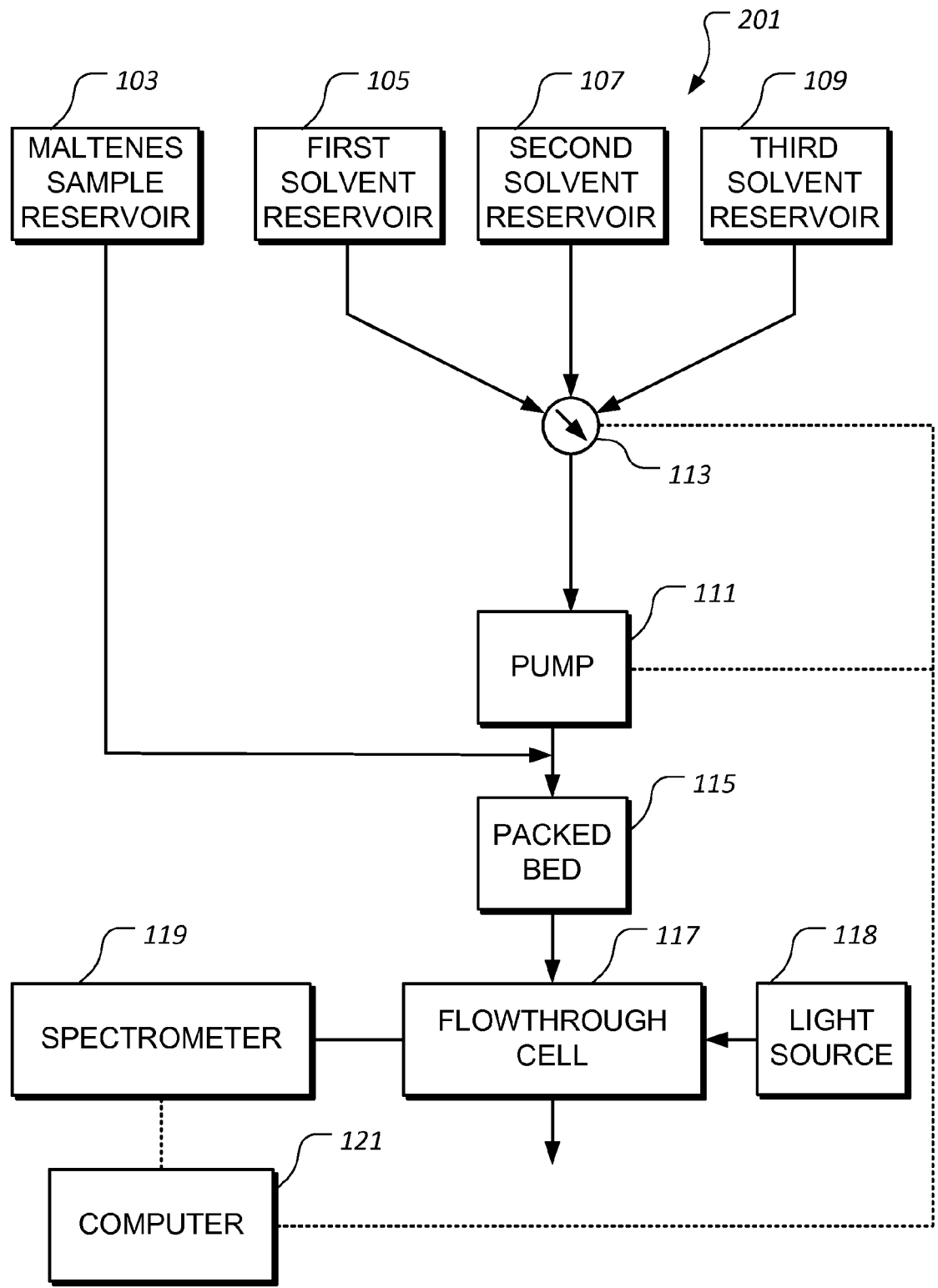
FIG. 2 is a schematic representation of a second illustrative embodiment of a system for characterizing crude oil fractions.

It should be noted that, in one embodiment, computer 121 is operably associated with one or more of pump 111, valve 113, and spectrometer 119 in a system 201, as shown in FIG. 2, such that computer 121 operates one or more of pump 111, valve 113, and spectrometer 119.

Figure 3:
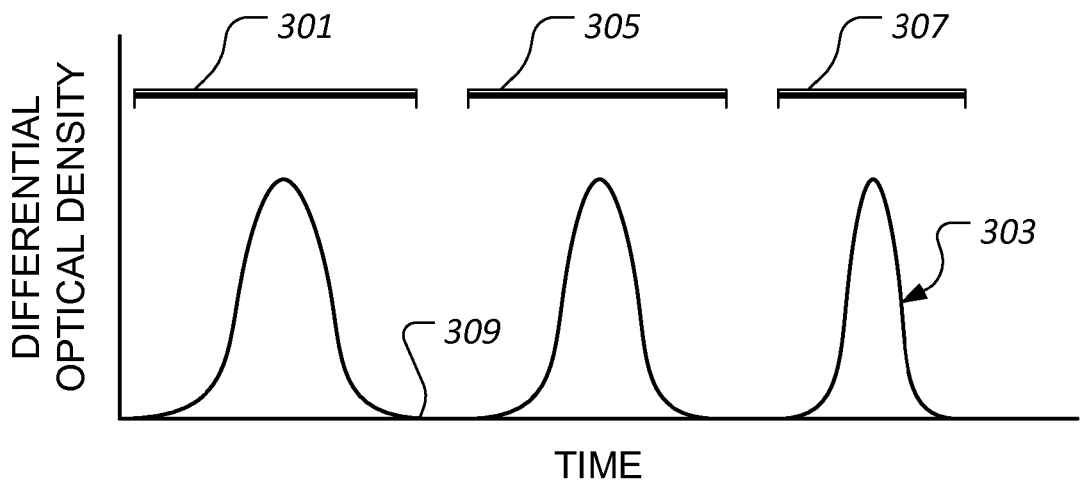
FIG. 3 is graphical representation of differential optical densities of maltene fractions with respect to time.

Utilizing flowthrough cell 117 in system 101 allows measurement of the differential optical density of each fraction, that is, the saturate fraction, the aromatic fraction, and the resin fraction, of the maltenes sample in real time. FIG. 3 depicts an illustrative, graphical representation of the differential optical densities of the maltene fractions with respect to time as they pass through flowthrough cell 117 and are measured by spectrometer 119 at, for example, the optical wavelengths disclosed herein. In the example shown in FIG. 3, a portion 301 of a curve 303 represents the saturates fraction of the maltenes, whereas portion 305 represents the aromatics fraction of the maltenes, and portion 307 represents the resins fraction of the maltenes. One can discern when a particular fraction has been generally completely eluted when the differential optical density of the fluid flowing through flowthrough cell 117 drops to near a baseline level after being elevated for a period of time. For example, generally all the saturates of the maltenes have been eluted when the data represented by a point 309 on curve 303 approaches the baseline level. The integral over each curve portion 301, 305, and 307, that is the area below each curve portion 301, 305, and 307, reveals the total concentration of each fraction. The total concentration and the area under each curve portion 301, 305, and 307 are correlated to quantify each fraction.

Figure 4:
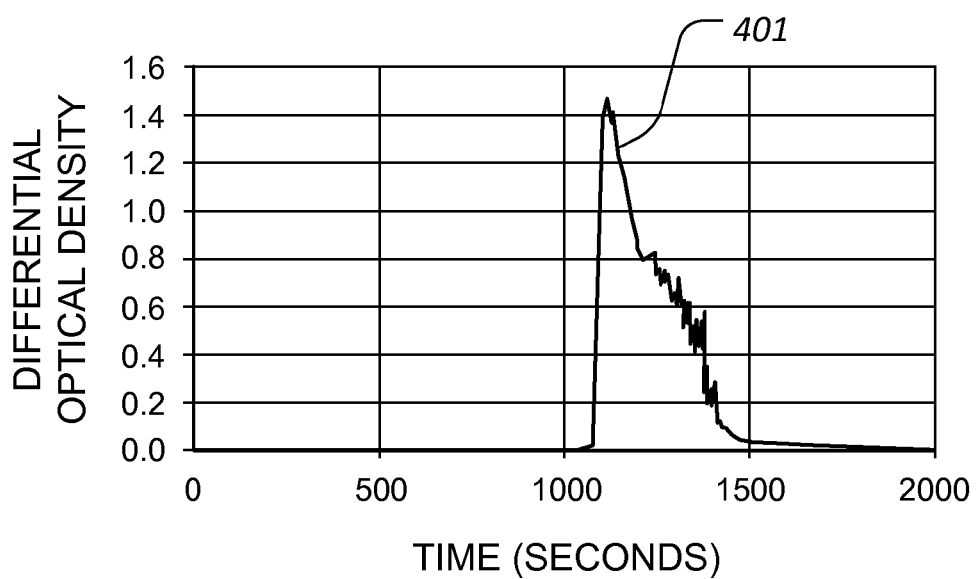
FIG. 4 is an example curve representing differential optical density data for a particular elution of an aromatic fraction with respect to time.
Figure 5:
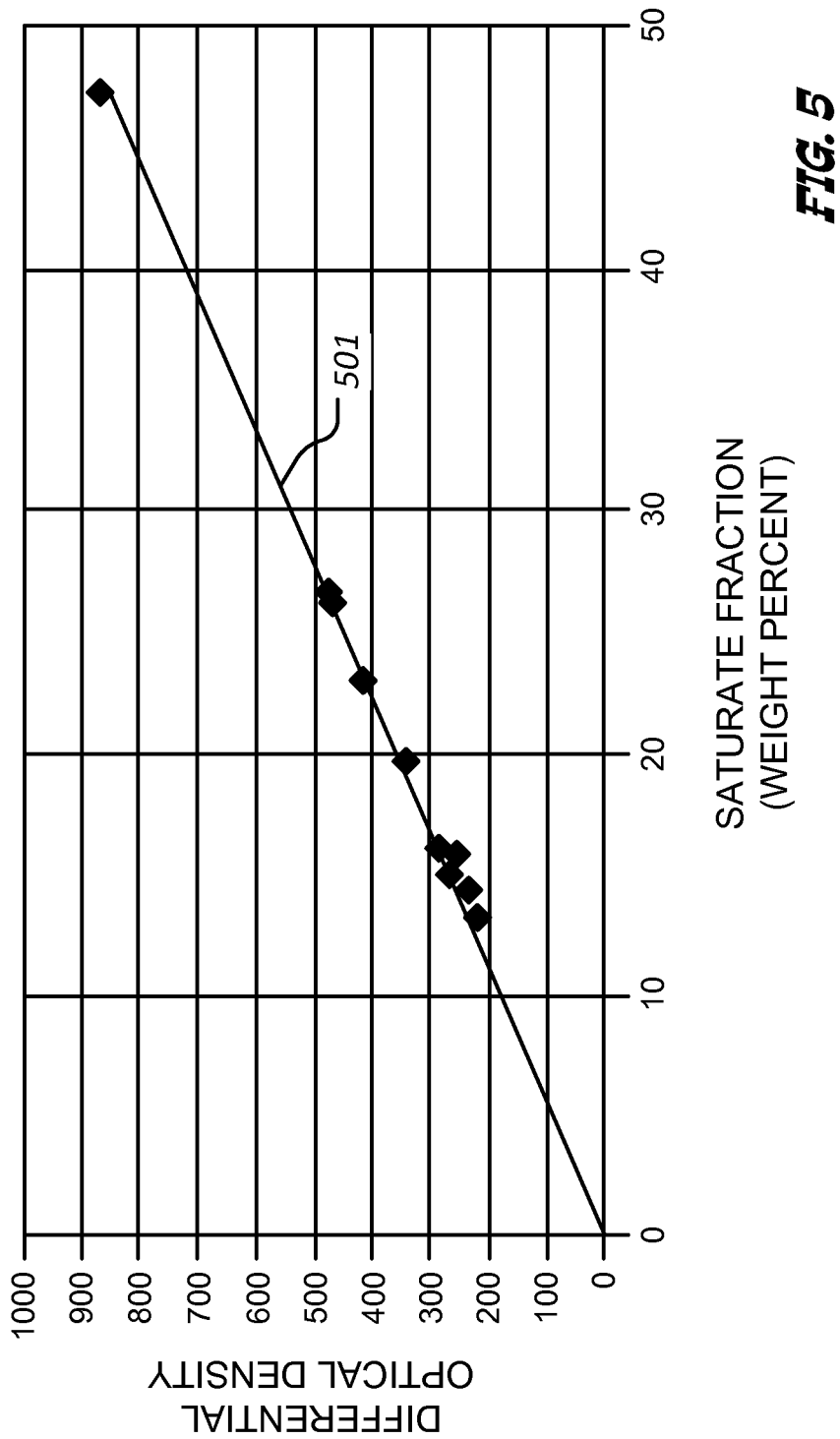
FIG. 5 is a graphical representation of correlations between the saturate fractions from a variety of crude oil maltenes and differential optical densities of the saturate fractions.
Figure 6:
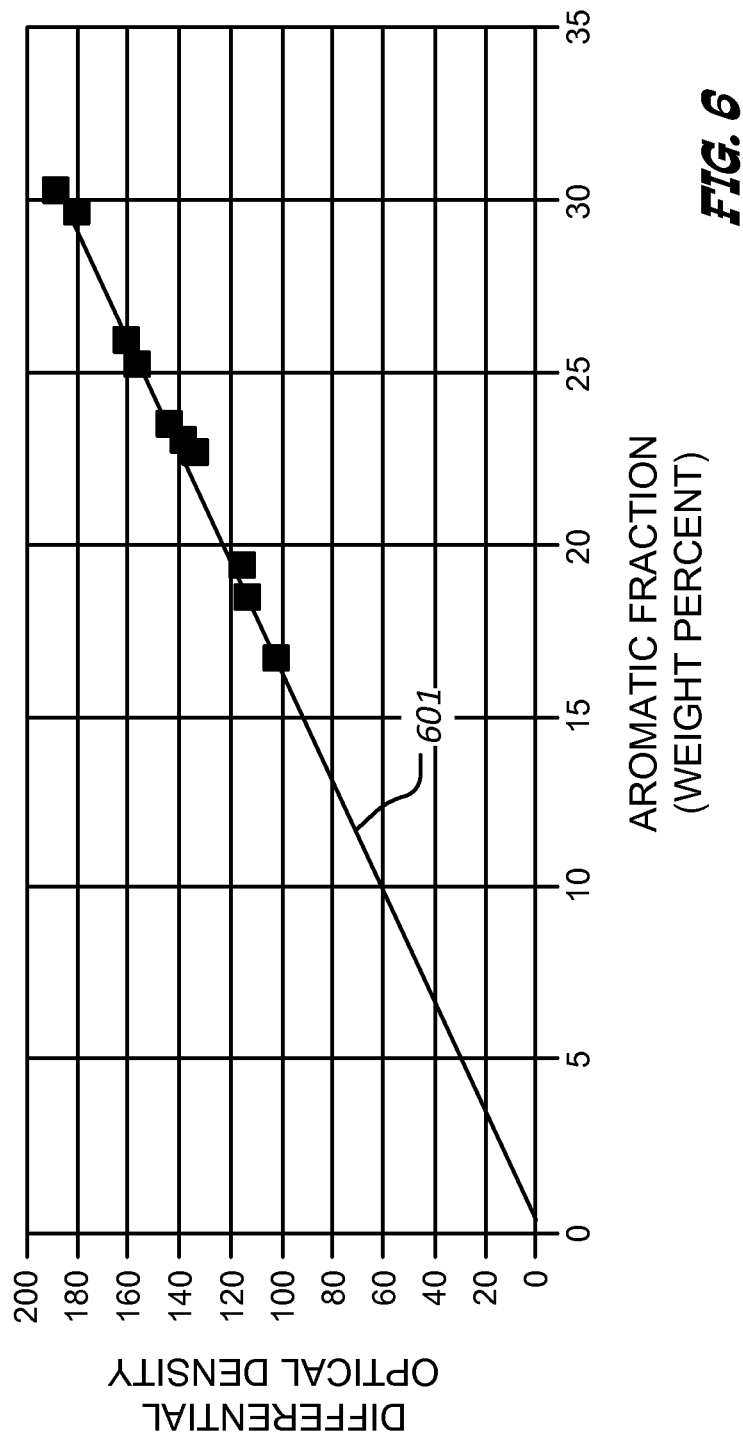
FIG. 6 is a graphical representation of correlations between the aromatic fractions from a variety of crude oil maltenes and differential optical densities of the aromatic fractions.
Figure 7:
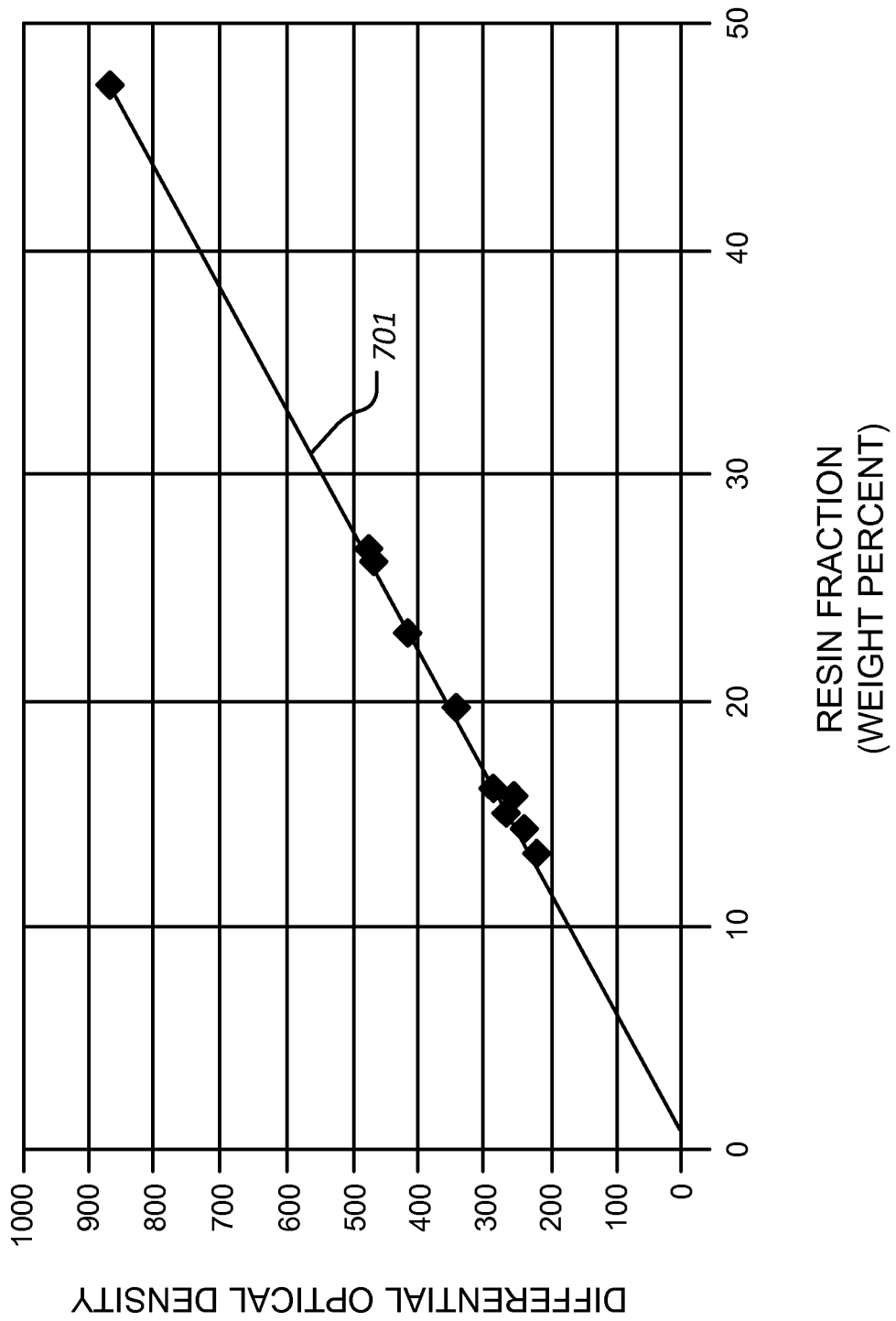
FIG. 7 is a graphical representation of correlations between the resin fractions from a variety of crude oil maltenes and differential optical densities of the resin fractions.

To generate such correlations, the saturate, aromatic, and resin fractions are collected while monitoring the optical density at wavelengths of about 285 nanometers, about 470 nanometers, and about 600 nanometers, respectively, as discussed herein. The optical densities are measured over time as the fractions are eluted. FIG. 4 depicts an example curve 401 of the differential optical density data for a particular elution of an aromatic fraction with respect to time. In one particular operation, the solvent flow rate for eluting the saturate fraction is about 5.0 milliliters per minute, while the solvent flow rates for eluting the aromatic and resin fractions are about 0.5 milliliters per minute. After each fraction is collected, the solvent in each fraction is evaporated and the concentration of each fraction is measured. FIGS. 5-7 depict graphical representations of correlations between the saturate, aromatic, and resin fractions, respectively, from a variety of crude oil maltenes and the integral over each differential optical density curve portion, for example, portions 301, 305, and 307 in FIG. 3, of the variety of crude oil maltenes. Lines 501, 601, and 701 in FIGS. 5, 6, and 7, respectively, represent best-fit linear curves based upon the data points, illustrating that the optical techniques of the present disclosure are sufficiently accurate for a wide variety of crude oil types.

Figure 8:
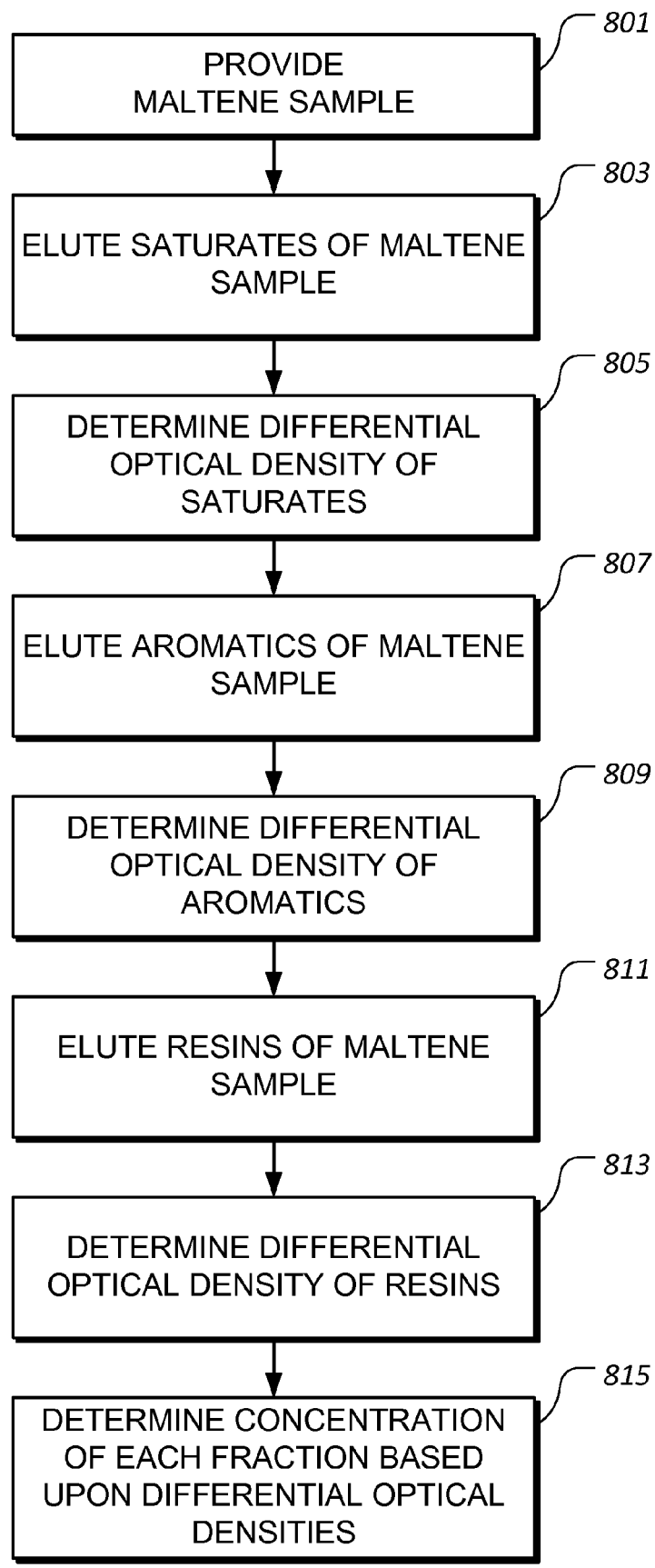
FIG. 8 is a flowchart representing a method for characterizing crude oil fractions.

Accordingly, an illustrative embodiment of a method for characterizing crude oil fractions is shown in FIG. 8. In the illustrated embodiment, a maltene sample is provided (block 801). Saturates of the maltene sample are eluted (block 803) using a solvent and the differential optical density of the saturates is determined over time as the saturates are eluted (block 805). In one embodiment, it is determined that the saturates have been sufficiently eluted when the differential optical density of the eluate generally approaches a baseline value. Aromatics of the maltene sample are eluted (block 807) using a solvent and the differential optical density of the aromatics is determined (block 809). In one embodiment, it is determined that the aromatics have been sufficiently eluted when the differential optical density of the eluate generally approaches a baseline value. Resins of the maltene sample are eluted (block 811) using a solvent and the differential optical density of the resins is determined (block 813). In one embodiment, it is determined that the resins have been sufficiently eluted when the differential optical density of the eluate generally approaches a baseline value. The concentration of each fraction, that is, each of the saturates, aromatics, and resins, is determined based upon the differential optical density of each fraction (block 815).

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

What is claimed is:

1. A system for characterizing crude oil fractions, comprising:
   a maltenes sample reservoir;
   a first solvent reservoir;
   a second solvent reservoir;
   a third solvent reservoir;
   a first pump in fluid communication with the first sample reservoir;
   a second pump in fluid communication with the second sample reservoir;
   a third pump in fluid communication with the third sample reservoir;
   a packed bed in fluid communication with each of the first, second, and third pumps and the maltenes sample reservoir;
   a flowthrough cell in fluid communication with the packed bed; and
   a spectrometer and light source operably associated with the flowthrough cell.

2. The system of claim 1, further comprising a computer operably associated with the spectrometer.

3. A system for characterizing crude oil fractions, comprising:
   a maltenes sample reservoir;
   a first solvent reservoir;
   a second solvent reservoir;
   a third solvent reservoir;
   a valve in fluid communication with the first solvent reservoir, the second solvent reservoir, and the third solvent reservoir;
   a pump in fluid communication with the valve;
   a packed bed in fluid communication with the pump and the maltenes sample reservoir;
   a flowthrough cell in fluid communication with the packed bed; and
   a spectrometer and light source operably associated with the flowthrough cell.

4. The system of claim 3, further comprising a computer operably associated with the spectrometer.

5. The system of claim 3, wherein:
   the first solvent reservoir is configured to store a solvent that is suitable to elute saturates of the maltenes;
   the second solvent reservoir is configured to store a solvent that is suitable to elute aromatics of the maltenes; and
   the third solvent reservoir is configured to store a solvent that is suitable to elute resins of the maltenes.

6. The system of claim 3, wherein:
   the first solvent reservoir stores a solvent that is suitable to elute saturates of the maltenes;
   the second solvent reservoir stores a solvent that is suitable to elute aromatics of the maltenes; and
   the third solvent reservoir stores a solvent that is suitable to elute resins of the maltenes.

7. The system of claim 6, wherein the solvent that is suitable to elute the saturates of the maltenes is n-heptane.

8. The system of claim 6, wherein the solvent that is suitable to elute the aromatics of the maltenes is toluene.

9. The system of claim 6, wherein the solvent that is suitable to elute the resins of the maltenes is a mixture of dichloromethane and methanol.

10. The system of claim 3, wherein the packed bed comprises an alumina or silica packed bed.

11. The system of claim 4, wherein the computer is operably associated with the valve.

12. The system of claim 4, wherein the computer is operably associated with the pump.

13. The system of claim 4, wherein the computer is operable to determine a concentration of each the eluted saturates, the eluted aromatics, and the eluted resins based upon optical densities over time for each of the eluted saturates, aromatics, and resins.

14. A method for characterizing crude oil fractions, comprising:
providing a maltene sample;
eluting saturates of the maltene sample;
determining an optical density of the saturates;
eluting aromatics of the maltene sample;
determining an optical density of the aromatics;
eluting resins of the maltene sample;
determining an optical density of the resins; and
determining a concentration of each of the eluted saturates, the eluted aromatics, and the eluted resins based upon optical densities over time for each of the eluted saturates, aromatics, and resins.

15. The method of claim 14, wherein eluting the saturates of the maltene sample comprises eluting the saturates of the maltene sample using n-heptane.

16. The method of claim 14, wherein eluting the aromatics of the maltene sample comprises eluting the aromatics of the maltene sample using toluene.

17. The method of claim 14, wherein eluting the resins of the maltene sample comprises eluting the resins of the maltene sample using a mixture of dichloromethane and methanol.

18. The method of claim 14, wherein determining the optical density of the saturates, determining the optical density of the aromatics, and determining the optical density of the resins is carried out using a flowthrough cell.

19. The method of claim 14, wherein eluting the saturates of the maltene sample, eluting the aromatics of the maltene sample, and eluting the resins of the maltene sample is carried out using a packed bed.

20. The method of claim 14, wherein determining the concentration of each of the eluted saturates, the eluted aromatics, and the eluted resins based upon the optical density of each of the eluted saturates, aromatics, and resins is carried out using an integral over a curve representing the optical density over time for each of the eluted saturates, aromatics, and resins.

21. The method of claim 14, wherein determining the concentration of each of the eluted saturates, the eluted aromatics, and the eluted resins based upon the optical density of each of the eluted saturates, aromatics, and resins is carried out using a predetermined correlation between optical density and concentration for each of the eluted saturates, aromatics, and resins.

22. The method of claim 14, wherein eluting the saturates of the maltene sample, eluting the aromatics of the maltene sample, and eluting the resins of the maltene sample is determined to be sufficiently complete when the optical density of an eluate generally approaches a baseline value.

23. A method for characterizing crude oil fractions, comprising:
providing a maltene sample;
eluting saturates of the maltene sample using an alumina packed bed and n-heptane;
determining optical densities over time for the saturates as the saturates are eluted;
eluting aromatics of the maltene sample using an alumina packed bed and toluene;
determining optical densities over time for the aromatics as the aromatics are eluted;
eluting resins of the maltene sample using an alumina packed bed and a mixture of dichloromethane and methanol;
determining optical densities over time for the resins as the resins are eluted; and
determining a concentration of each of the eluted saturates, the eluted aromatics, and the eluted resins based upon optical densities over time for each of the eluted saturates, aromatics, and resins.

* * * * *